(12) United States Patent
Chheda et al.

(10) Patent No.: US 8,889,384 B2
(45) Date of Patent: *Nov. 18, 2014

(54) PROCESS FOR THE PRODUCTION OF ALCOHOLS FROM BIOMASS

(75) Inventors: Juben Nemchand Chheda, Houston, TX (US); Evert Van Der Heide, Amsterdam (NL); Allison Elaine Falender, Houston, TX (US)

(73) Assignee: Shell Oil Company, Houston, TX (US)

( * ) Notice: Subject to any disclaimer, the term of this patent is extended or adjusted under 35 U.S.C. 154(b) by 246 days.

This patent is subject to a terminal disclaimer.

(21) Appl. No.: 13/252,872

(22) Filed: Oct. 4, 2011

(65) Prior Publication Data
US 2012/0107887 A1 May 3, 2012

Related U.S. Application Data

(60) Provisional application No. 61/390,870, filed on Oct. 7, 2010.

(51) Int. Cl.
*C12P 7/02* (2006.01)

(52) U.S. Cl.
USPC .......................................................... 435/155

(58) Field of Classification Search
None
See application file for complete search history.

(56) References Cited

U.S. PATENT DOCUMENTS

| | | | |
|---|---|---|---|
| 3,888,727 A | 6/1975 | Kenig | |
| 4,070,232 A | 1/1978 | Funk | 162/16 |
| 4,520,105 A | 5/1985 | Sinner et al. | |
| 4,668,340 A | 5/1987 | Sherman | |
| 5,536,325 A | 7/1996 | Brink | 127/43 |
| 5,726,046 A | 3/1998 | Farone et al. | 435/100 |
| 5,789,210 A | 8/1998 | Ho et al. | 435/163 |
| 6,299,774 B1 | 10/2001 | Ainsworth et al. | |
| 6,475,768 B1 | 11/2002 | Otero et al. | 435/233 |
| 6,663,777 B2 | 12/2003 | Schimel | |
| 7,402,224 B1 | 7/2008 | Avignon et al. | |
| 2002/0069987 A1 | 6/2002 | Pye | |
| 2003/0162271 A1 | 8/2003 | Zhang et al. | 435/161 |
| 2004/0237854 A1 | 12/2004 | Piretti | |
| 2005/0272134 A1 | 12/2005 | Hughes | |

(Continued)

FOREIGN PATENT DOCUMENTS

| | | |
|---|---|---|
| CN | 1160768 | 10/1997 |
| CN | 101158126 | 9/2008 |

(Continued)

OTHER PUBLICATIONS

Mosier et al., Features of promising technologies for pretreatment of lignocellulosic biomass, Bioresource Technology 96 (2005) 673-686.*

(Continued)

*Primary Examiner* — Karen Cochrane Carlson
*Assistant Examiner* — Jennifer M. H. Tichy

(57) ABSTRACT

Alcohols useful as fuel compositions are produced from biomass by: contacting the biomass with a cooking liquor containing 1 to 20 wt %, based on the cooking liquor, of sodium hydroxide, and under conditions effective to provide a pulp stream containing pulp having a lignin content of 5% to 20% by weight, based on the pulp washing the pulp stream; hydrolyzing the washed pulp stream with an enzyme solution; fermenting the hydrolyzate in the presence of a microorganism, one alcohol having 2 to 18 carbon atoms.

18 Claims, 2 Drawing Sheets

(56) References Cited

U.S. PATENT DOCUMENTS

| | | | |
|---|---|---|---|
| 2007/0254348 A1 | 11/2007 | Retsina et al. | 435/161 |
| 2008/0029233 A1 | 2/2008 | Wingerson et al. | |
| 2008/0142176 A1 | 6/2008 | van Heiningen et al. | |
| 2008/0187973 A1 | 8/2008 | Viitanen et al. | 435/161 |
| 2008/0190013 A1 | 8/2008 | Argyropoulos | 44/307 |
| 2008/0196847 A1 | 8/2008 | Van Heiningen et al. | 162/9 |
| 2008/0216391 A1 | 9/2008 | Cortright et al. | |
| 2008/0286870 A1 | 11/2008 | Viitanen et al. | 435/471 |
| 2009/0145021 A1 | 6/2009 | Guay et al. | |
| 2010/0269990 A1 | 10/2010 | Dottori et al. | 162/21 |
| 2011/0154721 A1 | 6/2011 | Chheda et al. | |
| 2011/0282115 A1 | 11/2011 | Chheda et al. | |
| 2014/0024093 A1* | 1/2014 | Blackbourn et al. | 435/158 |

FOREIGN PATENT DOCUMENTS

| | | | |
|---|---|---|---|
| EP | 1727890 | 5/2008 | C12N 1/19 |
| WO | WO9513362 | 5/1995 | C12N 1/14 |
| WO | WO9742307 | 11/1997 | C12N 1/16 |
| WO | 9745430 | 12/1997 | |
| WO | 9963149 | 12/1999 | |
| WO | WO2006096130 | 9/2006 | C12N 1/19 |
| WO | WO2007028811 | 3/2007 | C12N 15/61 |
| WO | WO2007136762 | 11/2007 | C12N 1/100 |
| WO | WO2007146245 | 12/2007 | C13K 1/02 |
| WO | WO2008065433 | 6/2008 | C12P 7/10 |
| WO | 2008095098 | 8/2008 | |
| WO | WO2008119082 | 10/2008 | C12P 7/64 |
| WO | WO2008155639 | 12/2008 | D21C 3/02 |
| WO | WO2009086265 | 7/2009 | C08B 37/14 |
| WO | WO2009109631 | 9/2009 | C12N 9/92 |
| WO | 2010025241 | 3/2010 | |
| WO | WO2010060052 | 5/2010 | C12P 7/10 |
| WO | WO2010078391 | 7/2010 | C12P 7/10 |

OTHER PUBLICATIONS

Wang et al., Sodium hydroxide pretreatment and enzymatic hydrolysis of coastal Bermuda grass, Bioresource Technology (2010); Published online Jan. 1, 2010; Biological Systems Engineering: Papers and Publication. Paper 143. Accessed online at: digitalcommons.unl.edu/biosysengfacpub/143.*

Zhang et al., Alkali pretreatment and enzymatic hydrolysis of cattails form constructed wetlands, American Journal of Engineering and Applied Sciences 3.2:327. Science Publications. (Jun. 2010).*

U.S. Appl. No. 13/332,276, filed Dec. 20, 2011, Chheda et al.

Gary A. Smook, Handbook for Pulp & Paper Technologists, published in 2002 by Angus Wilde Publications Inc., Vancouver, B.C., pp. 75-99.

Wang, Z., et al., "Sodium Hydroxide Pretreatment and Enzymatic Hydrolysis of Coastal Bermuda Grass", University of Nebraska—Lincoln, Bioresource Technology, 2010, pp. 1-3.

Zhang, B., et al., "Alkali Pretreatment and Enzymatic Hydrolysis of Cattails from Constructed Wetlands", 2010, American Journal of Engineering & Applied Sciences, vol. 2, Issue 2, pp. 328-332.

Chen M et al "Comparison of four different chemical pretreatments of corn stover for enhancing enzymatic digestibility" Biomass and Bioenergy, Pergamon, Amsterdam, NL, vol. 33, No. 10, Oct. 1, 2009, pp. 1381-1385.

McIntosh, S, et al: Optimisation of dilute alkaline pretreatment for enzymatic sacchartification of wehat straw, Biomass and Bioenergy, vol. 35, No. 7, Jul. 1, 2011, pp. 3094-3103.

* cited by examiner

PROCESS FOR THE PRODUCTION OF ALCOHOLS FROM BIOMASS

The present application claims the benefit of U.S. Provisional Patent Application Ser. No. 61/390,870, filed Oct. 7, 2010 the entire disclosure of which is hereby incorporated by reference.

FIELD OF THE INVENTION

This invention relates to a process for the production of alcohols from cellulosic biomass.

BACKGROUND OF THE INVENTION

The basic feedstocks for the production of first generation biofuels are often seeds, like grains such as wheat and corn, that produce starch or sugar cane and sugar beets that produce sugars that is fermented into bioethanol. However, the production of ethanol from these feedstocks suffers from the limitation that much of the farmland which is suitable for their production is already in use for food production.

Biologically produced alcohols, most commonly ethanol, and less commonly propanol and butanol, can be produced by the action of enzymes and microorganisms through the hydrolysis of starches or celluloses to glucose and subsequently fermentation of sugars. Cellulosic ethanol production uses non-food crops and does not divert food away from the food chain or inedible waste products which does not change the area of farmland in use for food products. However, production of ethanol from cellulose poses a difficult technical problem. Some of the factors for this difficulty are the physical density of lignocelluloses (like wood) that can make penetration of the biomass structure of lignocelluloses with chemicals difficult and the chemical complexity of lignocelluloses that lead to difficulty in breaking down the long chain polymeric structure of cellulose into sugars that can be fermented. Thus, it requires a great amount of processing to make the sugar monomers available to the microorganisms that are typically used to produce ethanol by fermentation.

Lignocellulose is the most abundant plant material resource and is composed mainly of cellulose, hemicelluloses and lignin. Woodchips are used in pulp and paper mills to convert wood into wood pulp by chemical or physical processes, usually Kraft process. In a Kraft process, woodchips are treated in a digester with a mixture of sodium hydroxide and sodium sulfide, known as white liquor. The woodchips are impregnated with a cooking solution that contains white liquor. White liquor is produced in the chemical recovery process.

In a continuous digester, the materials are fed at a rate which allows the pulping reaction to be complete by the time the materials exit the reactor. Typically delignification requires several hours at 155 to 175° C., typically around 170° C. Under these conditions lignin and some hemicelluloses degrade to give fragments that are soluble in the strongly basic white liquor. The solid pulp (about 50% by weight based on the dry wood chips) known as brown stock is collected and washed to produce brownstock pulp that typically contains 3 to 4% by weight lignin (Kappa #20-30) for softwood and 2 to 3% by weight lignin (Kappa #10-20) for hardwood, which is further passed through a series of bleaching steps to generate paper-quality pulp. The combined liquids known as black liquor contains extracted lignins, carbohydrates, sodium hydroxide, sodium sulfide and other inorganic salts. The black liquor is at about 15% solids and is concentrated in a multiple effect evaporator to 60% or even 75% solids and burned in the recovery boiler to recover the inorganic chemicals for reuse in the process. The combustion is carried out such that sodium sulfate, added as make-up is reduced to sodium sulfide by the organic carbon in the mixture. The molten salts from the recovery boiler are dissolved in process water known as "weak white liquor" composed of all liquors used to wash lime mud and green liquor precipitates. The resulting solution of sodium carbonate and sodium sulfide is known as "green liquor". Green liquor contains at least 4 wt %, typically 5 wt %, of sodium carbonate concentration. Green liquor is mixed with calcium hydroxide to regenerate the white liquor used in the pulping process.

Currently there exist two broad categories of processes for the hydrolysis of cellulose. One category uses mineral acids such as sulfuric acid as discussed in U.S. Pat. No. 5,726,046, while the second category uses enzymes. The mineral acid most commonly used in mineral acid process is sulfuric acid. In general sulfuric acid hydrolysis can be categorized as either dilute acid hydrolysis or concentrated acid hydrolysis.

The dilute acid processes generally involve the use of 0.5% to 15% sulfuric acid to hydrolyze the cellulosic material. In addition, temperatures ranging from 90° C. to 600° C., and pressure up to 800 psi are necessary to affect the hydrolysis. At high temperatures, the sugars degrade to form furfural and other undesirable by-products. The resulting fermentable sugar yields are generally low, less than 50% and process equipment must be employed to physically remove furfural before further processing.

The concentrated acid processes have been somewhat more successful, producing higher yields of sugar. However, these processes typically involve the use of 60% to 90% sulfuric acid to affect hydrolysis, leading to high cost due to the cost of handling concentrated sulfuric acid and it subsequent recovery.

The additional problems faced in the acid hydrolysis processes include the production of large amounts of gypsum when the spent or used acid is neutralized. The low sugar concentrations resulting from the processes require the need for concentration before fermentation can proceed. When hydrolysis is carried out at temperatures above 150° C., compounds such as furfural are produced from the degradation of pentoses. These compounds inhibit fermentation, and some may be toxic. Furthermore, the degradation of pentose sugars results in a loss of yield.

In a more recent development, production of ethanol from lignocellulosic biomass using green liquor pretreatment is described in WO2010/060052. However, the process does not render cellulose susceptible to enzymatic hydrolysis, and hence high glucose yields are not achieved. Acetic acid is only partially removed by this process which might lead to fermentation inefficiency.

SUMMARY OF THE INVENTION

Accordingly, one embodiment of the invention, a process for producing alcohol is provided comprising:
(a) providing a biomass containing cellulose fibers and at least 15 weight percent of lignin;
(b) contacting said biomass, in at least one digester, with a cooking liquor comprising 1 to 20 wt %, based on the cooking liquor, of sodium hydroxide, and water, wherein said cooking liquor having an active alkali of between 5 to 25%, and a sodium carbonate concentration of less than 3.5 wt % based on cooking liquor, at a cooking liquor to biomass ratio within the range of 2 to 6, at a temperature within the range of 100° C. to 230° C. with a residence time within 0.25 h to 4 h under conditions effective to provide a pulp stream containing pulp having a lignin content of 5% to 20% by weight, based on the pulp, and a chemical liquor stream containing sodium compounds;

(c) washing the pulp stream with a water stream thereby removing at least a portion of lignin and hemicellulosic material and producing washed pulp stream;

(d) hydrolyzing the washed pulp stream by treating the streams with an enzyme solution comprising cellulases and optionally xylanases at a pH within the range of about 3 to about 7 at a temperature within the range of 30° C. to 90° C. to produce a hydrolyzate containing from about 4% to 30% by weight of fermentable sugar;

(e) fermenting the hydrolyzate in the presence of a microorganism at a temperature with the range of about 25° C. to about 55° C. at a pH within the range of about 4 to about 6 thereby producing an alcohol stream containing at least one alcohol having 2 to 18 carbon atoms; and (f) recovering at least one of said alcohol from the alcohol stream.

In a further embodiment of the invention, in the process described above, the washed pulp stream from step (c) is concentrated by mechanical dewatering prior to contacting the washed pulp stream with cellulases in step (d) thereby increasing the solids content of the washed pulp stream to 15 to 40 wt % solids.

In another embodiment of the invention, the washed pulp stream is subjected to oxygen delignification prior to contacting the washed pulp stream with cellulases in step (d).

In another embodiment of the invention, solids in the washed pulp stream is mechanically refined prior to contacting the washed pulp stream with cellulases in step (d), thereby reducing the solids in size.

In another embodiment of the invention, the concentrated washed pulp stream is subjected to oxygen delignification prior to contacting the washed pulp stream with cellulases in step (d).

In another embodiment of the invention, the concentrated washed pulp stream is subjected to mechanically refining solids in the washed pulp stream prior to contacting the washed pulp stream with cellulases in step (d), thereby reducing the solids in size.

In another embodiment of the invention, the concentrated washed pulp stream is subjected to oxygen delignification and mechanically refining solids in the washed pulp stream prior to contacting the washed pulp stream with cellulases in step (d), thereby reducing the solids in size.

In another embodiment of the invention, the washed pulp stream is subjected to oxygen delignification and mechanically refining solids in the washed pulp stream prior to contacting the washed pulp stream with cellulases in step (d), thereby reducing the solids in size.

In yet another embodiment of the invention, in step (c) the water stream is flowing countercurrent to the pulp steam.

In yet another embodiment of the invention, at least a portion of the lignin is removed from one of washed pulp stream, hydrolyzate, or alcohol stream prior to step (d) or (e) thereby providing a washed pulp stream, hydrolyzate, or alcohol stream containing less than 5% lignin content based on said stream.

In yet another embodiment of the invention, the chemical liquor stream from step (b) is concentrated to produce a concentrated chemical liquor stream, the concentrated chemical liquor stream is burned to produce a chemical recycle stream, the chemical recycle stream is recausticized to produce a cooking liquor feed stream, and the cooking feed stream is recycled to the digester in step (b) as at least a portion of the cooking liquor.

In yet a further embodiment of the invention, at least a portion of the lignin is removed from the aqueous effluent stream to produce an aqueous effluent recycle stream which is recycled through the chemical recycle stream.

DETAILED DESCRIPTION OF THE INVENTION

It has now been found that by improving the digestive steps of biomass treatment and subsequent processing of such digestive product, a process with high yield production of alcohol suitable for use in fuel can be obtained. The invention process has significant benefits over other biomass pretreatments wherein the toxic components such as furfural and acetic acid are essentially eliminated for the fermentation process. Also, bulk removal of lignin allows improved mass transfer of enzymes to cellulose for conversion to fermentable sugars.

In some embodiments, the systems for performing the presently disclosed methods can be configured by repurposing the components of a pulp mill that previously used the Kraft pulping process. Such repurposing can allow for the employment of the presently disclosed methods with relatively low capital investment compared to many other proposed biomass-to-ethanol methods. Further, the control objective in a typical Kraft pulping is to cook to a target kappa number to correspond to lignin content of less than 4%. (see Handbook for Pulp & Paper Technologists, published in 2002 by Angus Wilde Publications Inc., Vancouver, B.C.). In the invention process, the digestion step is conducted under conditions that produce lignin content of 5 to 20%, preferably about 8 to about 18% then further processed in a manner to produce alcohol. It has been found that a process can be obtained to produce alcohol in high yields from biomass containing cellulosic fibers.

Figure 1:
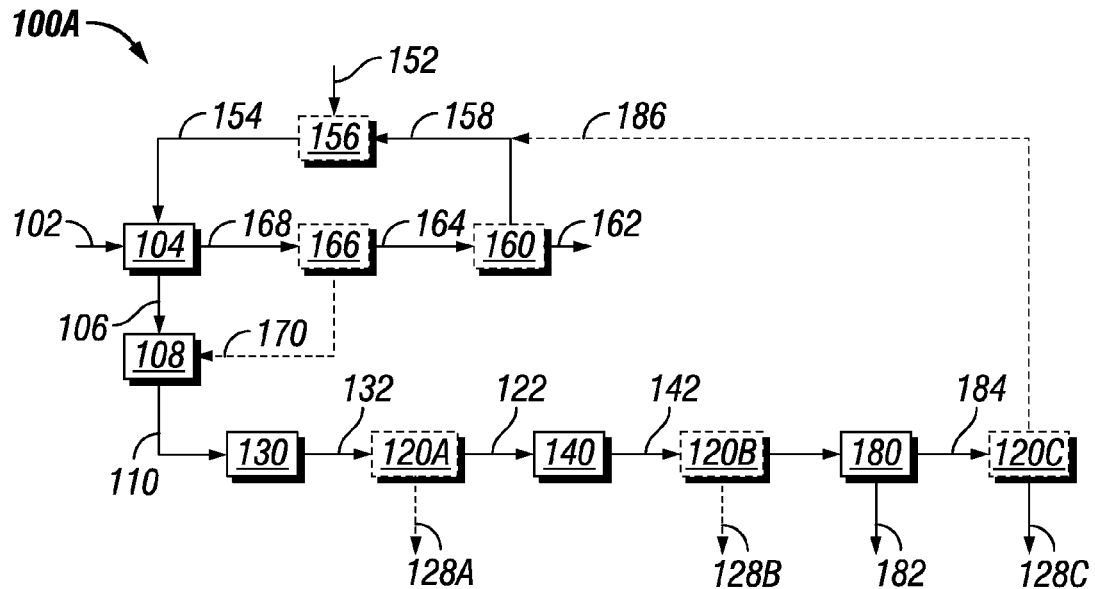
FIG. 1 shows a block schematic diagram illustrating one embodiment of the process of producing alcohol from biomass.
Figure 2:
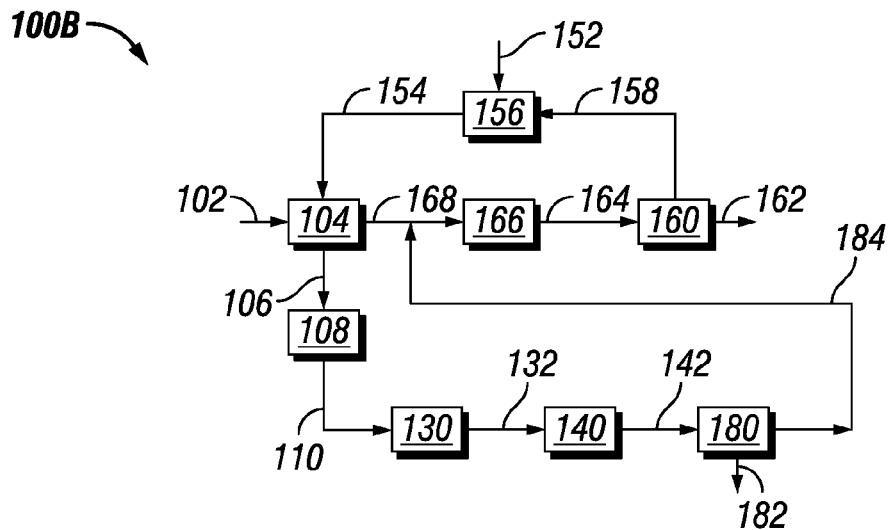
FIG. 2 shows a block schematic diagram illustrating another embodiment of the process of producing alcohol from biomass.
Figure 3:
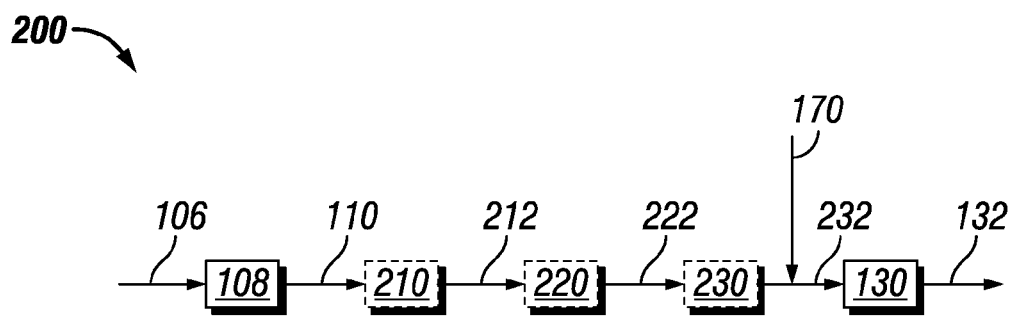
FIG. 3 shows a block schematic diagram illustrating yet another embodiment of the process of producing alcohol from biomass

The present process provides a method of producing an alcohol from a lignocellulosic biomass. In reference to FIG. 1, in one embodiment of the invention process 100A, biomass 102 is provided to digestion system 104 that may have one or more digester(s), whereby the biomass is contacted with a cooking liquor (optionally via cooking liquor feed stream 154) that was optionally at least a portion recycled from the recaustisized chemical recycle stream obtained from the chemical liquor stream 168 by concentrating the chemical liquor stream in a concentration system 166 thereby producing a concentrated chemical liquor stream 164 then burning the concentrated chemical liquor stream in a boiler system 160 thereby producing chemical recycle stream 158 and a flue gas stream 162, then converting the sodium containing compounds to sodium hydroxide in the recaustisizing system 156 by contacting with lime (CaO) 152 producing the cooking liquor feed stream 154 containing sodium hydroxide. Pulp stream 106 is obtained from the digestion system 104 by at least partially digesting the lignin and hemicelluloses in the biomass. The pulp stream 106 is then processed through a wash system 108 that may have one or more washing steps. Optionally, water recovered from the concentration system 166 can be recycled as wash water 170 to wash system 108. The thus-washed pulp stream 110 is provided to the enzymatic hydrolysis system 130 as feedstock or is then optionally concentrated by mechanical dewatering system 210 thereby producing high solids pulp stream 212 then provided to the enzymatic hydrolysis system 130. In the enzymatic hydrolysis system 130, pulp is hydrolyzed with an enzyme solution, whereby hydrolyzate (aqueous sugar stream) 132 is produced and fermented in the fermentation system 140 in the presence of a microorganism(s) to produce a fermented product stream containing at least one alcohol (alcohol stream 142). The alcohol 182 can then be recovered in a recovery system 180 from the alcohol stream 142 also producing aqueous effluent stream 184. Lignin can be optionally removed after the hydrolysis system, after the fermentation system or after the recovery system by lignin separation system 120, a, b, c, respectively removing lignin as a wet solid residue 128 a, b, c. The aqueous effluent stream after the removal of lignin can be optionally recycled as aqueous effluent recycle stream 186 to the chemical recycle stream 158 thereby reducing fresh water intake in the overall process. Optionally, the aqueous effluent recycle stream 186 can be recycled as wash water to wash system 108. In reference to FIG. 2, in another embodiment of the invention process, the aqueous effluent stream 184 can be recycled without the lignin separation system to the chemical liquor stream 168 and recycled and processed as described above. In reference to FIG. 3, in another embodiment of the invention process, the washed pulp stream 110 is optionally concentrated by mechanical dewatering system 210 thereby producing high solids pulp stream 212 then provided to the enzymatic hydrolysis system 130. The washed pulp stream 110 or the high solids pulp stream 212 is optionally delignified in the oxygen delignification system 220 thereby producing delignified pulp stream 222 then provided to the enzymatic hydrolysis system 130. In another embodiment the washed pulp stream 110, the high solids pulp stream 212 or the delignified pulp stream 222 is optionally mechanically refined in the mechanical refining system 230 thereby producing a refined pulp stream 232 then provided to the enzymatic hydrolysis system 130. Any of 210, 220 or 230 system can be optionally used in any combination of one, two or three process combinations. The Figures are included as an example of how the present invention can be practiced and is not meant to be limiting in any manner.

Any suitable (e.g., inexpensive and/or readily available) type of biomass can be used. Suitable lignocellulosic biomass can be, for example, selected from, but not limited to, forestry residues, agricultural residues, herbaceous material, municipal solid wastes, waste and recycled paper, pulp and paper mill residues, and combinations thereof. Thus, in some embodiments, the biomass can comprise, for example, corn stover, straw, bagasse, miscanthus, sorghum residue, switch grass, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like.

Prior to pretreatment with the cooking liquor, the biomass can be washed and/or reduced in size (e.g., chopping, crushing or debarking) to a convenient size and certain quality that aids in moving the biomass or mixing and impregnating the chemicals from cooking liquor. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

In the digestion system, the size-reduced biomass is contacted with the cooking liquor in at least one digester where the pretreatment reaction takes place. The cooking liquor contains (i) at least 1 wt %, more preferably at least 4 wt %, to 20 wt %, more preferably to 10 wt %, based on the cooking liquor, of sodium hydroxide, (ii) optionally 0 to 20 wt %, based on the cooking liquor, of sodium sulfide; (iii) optionally, 0 to 3%, based on the cooking liquor, of anthraquinone, sodium borate and/or polysulfides; and (iv) water (as remainder of the cooking liquor). The cooking liquor should have an active alkali of between 5 to 25%, more preferably between 10 to 20%. The term "active alkali"(AA), as used herein, is a percentage of NaOH plus $Na_2S$, if any, expressed as $Na_2O$ based on weight of the biomass less water content (dry solid biomass). The cooking liquor has a sodium carbonate concentration of less than 3.5 wt % based on cooking liquor, preferably less than about 2.0 wt %. The cooking liquor contains sodium hydroxide, sodium sulfide and/or any combination with less than 3.5 wt % of sodium carbonate. If sodium sulfide is present in the cooking liquor, the sulfidity can range from about 15% to about 40%, preferably from about 20 to about 30%. The term "sulfidity", as used herein, is a percentage ratio of $Na_2S$, expressed as $Na_2O$, to active alkali. The cooking liquor to biomass ratio can be within the range of 2 to 6, preferably 3 to 5. The pretreatment reaction is carried out at a temperature within the range of 100° C. to 230° C., and a residence time within 0.25 h to 4 h. The reaction is carried out under conditions effective to provide a pulp stream containing pulp having a lignin content of 5% to 20% by weight, based on the pulp, and a chemical liquor stream containing sodium compounds and dissolved lignin and hemicelluloses material.

Unlike in the "dilute acid" processes, the digester can be a lower cost made pressure vessel of carbon steel or stainless steel or similar alloy. The cooking can be done in continuous or batch mode. Suitable pressure vessels include, but are not limited to the "PANDIA™ Digester" (Voest-Alpine Industrienlagenbau GmbH, Linz, Austria), the "DEFIBRAOR Digester" (Sunds Defibrator AB Corporation, Stockholm, Sweden), M&D (Messing & Durkee) digester (Bauer Brothers Company, Springfield, Ohio, USA) and the KAMYR Digester (Andritz Inc., Glens Falls, N.Y., USA). The cooking liquor has a pH from 10 to 14, preferably around 12 to 13 depending on AA. The contents can be kept at a temperature within the range of from 100° C. to 230° C. for a period of time, more preferably within the range from about 130° C. to about 180° C. The period of time can be from about 0.25 to 4.0 hours, preferably from about 0.5 to about 2 hours, after which the pretreated contents of the digester are discharged. For adequate penetration, a sufficient volume of liquor is required to ensure that all the chip surfaces are wetted. Sufficient liquor is supplied to provide the specified alkali charge as defined by AA. The effect of greater dilution is to decrease the concentration of active chemical and thereby reduce the reaction rate. It is important that the lignin content of the pre-treated stream (pulp stream) is controlled between 5% to 20% by weight, preferably 5% to 17% by weight, more preferably from 10% to 15% by weight, based on the pulp.

The reaction happening during the cook are complex and not totally understood. It is believed that sufficient time must be provided to achieve good cooking liquor penetration into the biomass such as chips before the main reaction occur. Swelling agent such as sodium hydroxide has at least six times higher rate of diffusion compared to other chemicals such as sodium carbonate and sodium sulfide, which significantly improves the reaction rates. Chip thickness is therefore an important parameter to cooking liquor impregnation if wood is the biomass source to allow sufficient cooking liquor penetration into the chips. Essentially, the swollen lignin in the biomass is chemically split into fragments by the hydroxyl ions (OH—) and hydrosulfide (SH—) ions present in the cooking liquor. The lignin fragments are then dissolved as phenolate or carboxylate ions. The dissolved lignin has the tendency to undergo condensation reaction that is difficult to remove from the fibers, thereby leading to lower enzymatic activity during the subsequent hydrolysis reaction. However, the presence of hydrosulfide ions from sodium sulfide reduce the condensation reactions by blocking the reactive groups. The bulk delignification happens as a first order reaction. The acetyl groups also get neutralized during the reaction to form sodium salts thereby removing the toxic component for fermentation of sugars to alcohol in the cooking liquor. Carbohydrates, primarily hemicelluloses, and some cellulose, are also chemically attacked and dissolved to some extent. Additionally, the hemicelluloses removed during the pretreatment reaction does not degrade to toxic furan compounds due to alkaline nature of the cooking medium. Thus, the invention process has significant benefits over other acidic pretreatments wherein the toxic components such as furfural and acetic acid are essentially eliminated for the fermentation system. Also, bulk removal of lignin allows improved mass transfer of enzymes to cellulose for conversion to fermentable sugars and lower equipment and energy requirements due to smaller volumes going forward. In a typical reaction, about 70% by weight of the feed lignin, 50% by weight of hemicelluloses and about 10% by weight of celluloses is dissolved during the cooking reaction. Depending on the AA of the cooking liquor the amount of total biomass dissolved can range from 25% to 55% by weight, more preferably from about 35 to about 45%.

In some embodiments, the pretreatment could further comprise the use of one or more additives to increase the yield of carbohydrates. Such additives include, but are not limited to, anthraquinone, sodium borate and sodium polysufides and combinations thereof.

In the wash system, the pulp stream can be washed to remove one or more of non-cellulosic material, non-fibrous cellulosic material, and non-degradable cellulosic material prior to enzymatic hydrolysis. The pulp stream is washed with water stream under conditions to remove at least a portion of lignin and hemicellulosic material in the pulp stream and producing washed pulp stream having solids content of 5% to 15% by weight, based on the washed pulp stream. For example, the pulp stream can be washed with water to remove dissolved substances, including degraded, but non-fermentable cellulose compounds, solubilised lignin, and/or any remaining alkaline chemicals such as sodium compounds that were used for cooking or produced during the cooking (or pretreatment). The washed pulp stream may contain higher solids content by further processing such as mechanical dewatering as described below.

Figure 4:
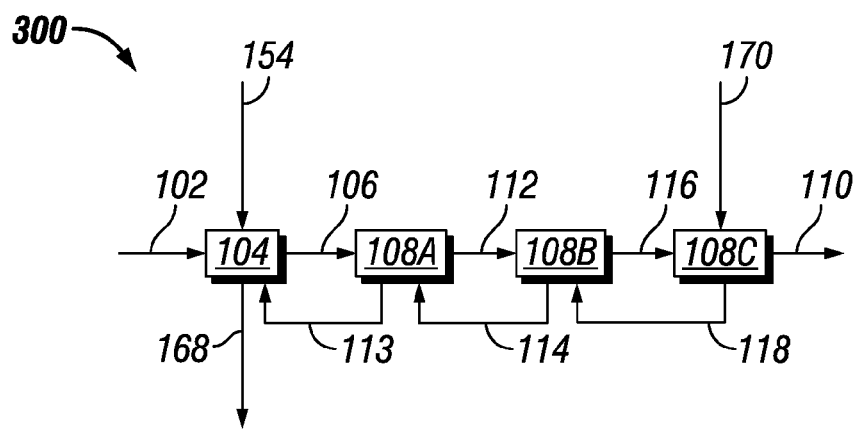
FIG. 4 shows a block schematic diagram illustrating the countercurrent washing embodiment of the process.

In a preferred embodiment, the pulp stream is washed counter-currently. The wash can be at least partially carried out within the digester and/or externally with separate washers. In reference to FIG. 4, in one embodiment of the invention process, the wash system contains more than one wash steps, for example, 108*a* first washing, 108*b* second washing, 108*c* third washing, etc. that produces washed pulp stream from first washing 112, washed pulp stream from second washing 116, etc. operated in a counter current flow with the water, that is then sent to subsequent processes as washed pulp stream 110. The water is recycled through first recycled wash stream 118 and second recycled wash stream 114 and then to third recycled wash stream 113. Water recovered from the chemical liquor stream 168 by the concentration system 166 can be recycled as wash water 170 to wash system 108. It can be appreciated that the washed steps can be conducted with any number of steps to obtain the desired washed pulp stream. Additionally, the washing lowers the pH from highly alkaline environment to a pH level of about 8 to 10, which is important for subsequent hydrolysis step where the pH is about 5.

In some embodiments, the materials or chemicals can be regenerated thereby reducing the addition of fresh make-up chemical cost and lowering the load on the effluent plant. The recovery of chemicals and energy from the residual chemical liquor stream are integral part of the process. In one embodiment, a weak chemical liquor stream (about 15% solids), that can be obtained from the pulp wash system, from the digestive system, and optionally from a oxygen delignification unit, is concentrated through a series of evaporation and chemical addition steps into a heavy or concentrated chemical liquor at about 60-75% solids. Subsequently, the concentrated chemical liquor stream is incinerated (or burned) in the recovery furnace to form inorganic smelt. The lignin and the solubilised sugar components can be used as an energy source in this combustion step. In some embodiments, lignin collected following an enzymatic hydrolysis step can be optionally added to the concentrated chemical stream to increase the lignin content. In some embodiments, the lignin can be used as energy source to provide heat during the distillation of alcohol or any other step in the biomass-to-alcohol process. In some embodiments, the lignin can be co-fired as fuel for the lime-kiln in the recausticizing operation or in a power boiler for steam and power generation. The smelt from the furnace can be dissolved by addition of water or any recycle aqueous stream (for example, the aqueous effluent stream from bottoms of the distillation). The chemicals are then subjected to recausticizing operation where the chemicals are regenerated using burned lime to form the cooking liquor.

Optionally, the pretreated and washed biomass can be refined using any suitable mechanical refining device to further break down the material in size prior to enzymatic hydrolysis. For example, the contents of the pretreatment pressure vessel can be discharged into a mechanical disc refiner or PFI refiner (or other typical refiner used in the pulping industry) to break the cooked biomass open and reduce the cooked biomass to fibers that have improved enzymatic digestibility. In some embodiments, the refining can provide bundles of cellulose fibers, single cellulose fibers, fragments of cellulose fibers, or combinations thereof. In some embodiments, refining provides largely single fibers and bundles of single fibers. In some embodiments, refining can provide pretreated biomass wherein over 90% of the material is single fibers or fragments of single fibers.

Generally, not all the lignin is removed by the pretreatment reaction. In some embodiments, at least a portion of the residual lignin can be removed from the washed pulp stream by oxygen delignification. Accordingly, in some embodiments, solids from the pretreated lignocellulo sic mixture can be collected (via filtration or decanting of any liquids), dried and placed in an aqueous alkaline solution (e.g., water comprising 2% to 5% by weight of NaOH). The alkaline solution of solids can then be placed in a pressurized vessel and treated with oxygen gas at an elevated temperature, such as between about 60° C. and about 150° C., for a period of time effective to remove at least a portion of the lignin, such as between about 10 minutes to about 4 hours. In some embodiments, the lignin can then be removed via washing (e.g., in water). In some embodiments, oxygen delignification can be performed prior to a refining system, such that the final pretreated lignocellulosic biomass mixture (i.e., the biomass used for enzymatic hydrolysis and fermentation) is a mixture that has been treated with cooking liquor, washed, subjected to oxygen delignification, and refined. In an oxygen delignification system, a portion of the lignin is removed from one of washed pulp stream, hydrolyzate, or alcohol stream prior to step (d) or (e). The resulting washed pulp stream, hydrolyzate, or alcohol stream containing less than 5 wt % lignin content, more preferably less than 3 wt % lignin content, based on such stream.

Optionally, the washed pulp stream can be concentrated by mechanical dewatering to produce a high solids pulp stream having about 15% to 40 wt % solids. The mechanical dewatering can be carried out by any mechanical dewatering devices including, for example, filter presses, rotary washers and/or screw presses, to produce a high solids pulp stream having up to 40 wt % solids, more preferably up to 30 wt % solids. Higher consistency (or solids) pulp leads to concentrated beer stream at the back end, thereby lowing the equipment size for the hydrolysis/fermentation vessels reducing the capital cost and additionally saving on energy, e.g. 50% energy saving by distilling concentrated (10%) versus dilute beer stream (4%).

Optionally, following the pretreatment and/or any other desired pretreatment steps (washing, refining, oxygen delignifying, mechanical dewatering), the pretreated biomass and/or fibers can then be subjected to enzymatic hydrolysis for conversion to fermentable sugars. The enzymatic hydrolysis can be carried out at between about 5 and about 15% fiber consistency or at a higher consistency between 15 to 40%. In some embodiments, the lignocelluloses-degrading enzymes can be mixed with pretreated mixture at a fiber consistency of about 5% to about 15% for a few minutes (between 1-20 minutes), thickened using a filter press and allowed to hydrolyze for an additional period of time at the higher fiber consistency. Additional enzymes can be added to the thinned mixture. The term "fermentable sugar" refers to oligosaccharides and monosaccharides that can be used as a carbon source by a microorganism in a fermentation process.

In the enzymatic hydrolysis processes 130 the pH of the pretreated feedstock to the enzymatic hydrolysis is typically adjusted so that it is within a range which is optimal for the cellulose enzymes used. Generally, the pH of the pretreated feedstock is adjusted to within a range of about 3.0 to about 7.0, or any pH there between. For example, the pH may be within a range of about 4.0 to about 6.0, or any pH there between, more preferably between about 4.5 and about 5.5, or any pH there between, or about 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0 or any pH there between. Since the pretreated feedstock is alkaline, an acid such as, for example, sulfuric acid or nitric acid may be used for the pH adjustment.

The temperature of the pretreated feedstock is adjusted so that it is within the optimum range for the activity of the cellulose enzymes. Generally, a temperature of about 15° C. to about 100° C., about 30° C. to about 70° C. preferably or any temperature there between, is suitable for most cellulose enzymes, for example a temperature of 45, 46, 47, 48, 49, 50, 51, 52, 53, 54, 55° C., or any temperature there between. The cellulase enzymes and the β-glucosidase enzyme are added to the pretreated feedstock, prior to, during, or after the adjustment of the temperature and pH of the aqueous slurry after pretreatment. Preferably the cellulase enzymes and the β-glucosidase enzyme are added to the pretreated lignocellulosic feedstock after the adjustment of the temperature and pH of the slurry. By the term "cellulase enzymes" or "cellulases," it is meant a mixture of enzymes that hydrolyze cellulose. The mixture may include cellobiohydrolases (CBH), glucobiohydrolases (GBH), endoglucanases (EG), and β-glucosidase. In a non-limiting example, a cellulase mixture may include EG, CBH, and β-glucosidase enzymes. The EG enzymes primarily hydrolyzes cellulose polymer in the middle of the chain to expose individual cellulose chains. There are two types of CBH enzymes, CBHI and CBHII. CBHI and CBHII cleave the reducing and non-reducing end of the cellulose chains to produce cellobiose. The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC 3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. It is also contemplated that the β-glucosidase enzyme may be modified to include a cellulose binding domain, thereby allowing this enzyme to bind to cellulose.

The enzymatic hydrolysis may also be carried out in the presence of one or more xylanase enzymes. Examples of xylanase enzymes that may also be used for this purpose and include, for examples, xylanase 1, 2 (Xyn1 and Xyn2) and β-xylosidase, which are typically present in cellulase mixtures.

The process of the present invention can be carried out with any type of cellulase enzymes, regardless of their source. Non-limiting examples of cellulases which may be used in the practice of the invention include those obtained from fungi of the genera *Aspergillus, Humicola,* and *Trichoderma, Myceliophthora, Chrysosporium* and from bacteria of the genera *Bacillus* and *Thermobifida*. In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

The cellulase enzyme dosage is chosen to convert the cellulose of the pretreated feedstock to glucose. For example, an appropriate cellulase dosage can be about 0.1 to about 40.0 Filter Paper Unit(s) (FPU or IU) per gram of cellulose, or any amount there between, for example, 0.1, 0.5, 1.0, 2.0, 4.0, 6.0, 8.0, 10.0, 12.0, 14.0, 16.0, 18.0, 20.0, 22.0, 24.0, 26.0, 28.0, 30.0, 32.0, 34.0, 36.0, 38.0, 40.0 FPU (or IU) per gram of cellulose, or any amount. The term Filter Paper Unit(s) refers to the amount of enzyme required to liberate 2 mg of reducing sugar (e.g., glucose) from a 50 mg piece of Whatman No. 1 filter paper in 1 hour at 50° C. at approximately pH 4.8.

In practice, the hydrolysis is carried out in a hydrolysis system, which may include a series of hydrolysis reactors. The number of hydrolysis reactors in the system depends on the cost of the reactors, the volume of the aqueous slurry, and other factors. For a commercial-scale alcohol plant, the typical number of hydrolysis reactors may be 1 to 10, more preferably 2 to 5, or any number there between. In order to maintain the desired hydrolysis temperature, the hydrolysis reactors may be jacketed with steam, hot water, or other heat sources. Preferably, the cellulose hydrolysis is a continuous process, with continuous feeding of pretreated lignocellulosic feedstock and withdrawal of the hydrolysate slurry. However, it should be understood that batch processes are also included within the scope of the present invention. In one embodiment, a series of Continuous Stirred-Tank Reactor (CSTR) may be used for a continuous process. In another embodiment Short Contact—Time Reactor (SCTR) along with finishing reactor may be used. A thinning reactor may or may not be included in the hydrolysis system.

The enzymatic hydrolysis with cellulase enzymes produces an aqueous sugar stream (hydrolyzate) comprising glucose, unconverted cellulose and lignin. Other components that may be present in the hydrolysate slurry include the sugars xylose, arabinose, mannose and galactose, the organic acids acetic acid, glucuronic acid and galacturonic acid, as well as silica, insoluble salts and other compounds.

The hydrolysis may be carried out in two stages (see U.S. Pat. No. 5,536,325, which is incorporated herein by reference), or may be performed in a single stage.

In the fermentation system 140, the aqueous sugar stream is then fermented by one or more than one fermentation microorganism to produce a fermentation broth comprising the alcohol fermentation product. In one embodiment, the aqueous sugar stream sent to fermentation may be substantially free of undissolved solids, such as lignin and other unhydrolyzed components so that the later step of separating the microorganism from the fermentation broth will result in the isolation of mainly microorganism; for example, lignin removal step is carried out at 120a. The separation may be carried out by known techniques, including centrifugation, microfiltration, plate and frame filtration, crossflow filtration, pressure filtration, vacuum filtration and the like.

In the fermentation system, any one of a number of known microorganisms (for example, yeasts or bacteria) may be used to convert sugar to ethanol or other alcohol fermentation products. The microorganisms convert sugars, including, but not limited to glucose, mannose and galactose present in the clarified sugar solution to a fermentation product.

Many known microorganisms can be used in the present process to produce the desired alcohol for use in biofuels. Clostridia, *Escherichia coli* (*E. coli*) and recombinant strains of *E. coli*, genetically modified strain of *Zymomonas mobilis* such as described in US2003/0162271, US2008/0286870 and US2008/0187973 (which disclosures are herein incorporated by reference) are some examples of such bacteria. The microorganisms may further be a yeast or a filamentous fungus of a genus *Saccharomyces, Kluyveromyces, Candida, Pichia, Schizosaccharomyces, Hansenula, Kloeckera, Schwanniomyces, Yarrowia, Aspergillus, Trichoderma, Humicola, Acremonium, Fusarium*, and *Penicillium*.

In another embodiment, for example, the fermentation may be performed with recombinant yeast engineered to ferment both hexose and pentose sugars to ethanol. Recombinant yeasts that can ferment one or both of the pentose sugars xylose and arabinose to ethanol are described in U.S. Pat. Nos. 5,789,210, 6,475,768, European Patent EP 1,727,890, European Patent EPI 863,901 and WO 2006/096130 which disclosures are herein incorporated by reference. Xylose utilization can be mediated by the xylose reductase/xylitol dehydrogenase pathway (for example, WO9742307 A1 19971113 and WO9513362 A1 19950518) or the xylose isomerase pathway (for example, WO2007028811 or WO2009109631). It is also contemplated that the fermentation organism may also produce fatty alcohols, for example, as described in WO 2008/119082 and PCT/US07/011,923 which disclosure is herein incorporated by reference. In another embodiment, the fermentation may be performed by yeast capable of fermenting predominantly C6 sugars for example by using commercially available strains such as *Thermosacc* and *Superstart*.

Preferably, the fermentation is performed at or near the temperature and pH optima of the fermentation microorganism. For example, the temperature may be from about 25° to about 55° C., or any amount there between. A typical temperature range for the fermentation of sugar to alcohol using microorganisms is between about 25° C. to about 37° C. or any temperature there between, for example from 25, 26, 27, 28, 29, 30, 31, 32, 33, 34, 35, 36, 37° C. or any temperature there between, although the temperature may be higher if the microorganism is naturally or genetically modified to be thermostable. The pH of a typical fermentation employing microorganisms is between about 3 and about 6, or any pH there between, for example, a pH of 3.0, 3.5, 4.0, 4.5, 5.0, 5.5, 6.0, or any pH there between. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The sugar stream may also be supplemented with additional nutrients for growth of the fermentation microorganism. For example, yeast extract, specific amino acids, phosphate, nitrogen sources, salts, trace elements and vitamins may be added to the hydrolysate slurry to support growth and optimize productivity of the microorganism.

The fermentation may be conducted in batch, continuous or fed-batch modes, with or without agitation. The fermentation system may employ a series of fermentation reactors.

Preferably, the fermentation reactors are agitated lightly with mixing. In a typical commercial-scale fermentation, the fermentation may be conducted using a series of reactors, such as 1 to 6, or any number there between.

Optionally, the fermentation may be conducted so that the fermentation microorganisms are separated from the fermentation and sent back to the drawing fermentation reaction. This may involve continuously withdrawing fermentation broth from the fermentation reactor and separating the microorganism from this solution by known separation techniques to produce a microorganism slurry. Examples of suitable separation techniques include, but are not limited to, centrifugation, microfiltration, plate and frame filtration, crossflow filtration, pressure filtration, settling, vacuum filtration and the like.

In some embodiment, the hydrolysis system and fermentation system may be conducted in the same vessel. In one embodiment, the hydrolysis can be partially completed and the partially hydrolyzed stream may be fermented. In one embodiment, a simultaneous saccharification and fermentation (SSF) process where hydrolysis system may be run until the final percent solids target is met and then the hydrolyzed biomass may be transferred to a fermentation system.

The fermentation system produces an alcohol stream 142 containing at least one alcohol having 2 to 18 carbon atoms. In the recovery system 180, when the product to be recovered in the alcohol stream is a distillable alcohol, such as ethanol, the alcohol can be recovered by distillation in a manner known to separate such alcohol from an aqueous stream.

The alcohol stream (separated fermentation broth or beer) sent to the distillation is a dilute alcohol solution including unconverted cellulose and residual lignin. It may also contain components added during the fermentation to support growth of the microorganisms, as well as small amounts of microorganism that may remain after separation. The alcohol stream is preferably degassed to remove carbon dioxide and then pumped through one or more distillation columns to separate the alcohol from the other components. The column(s) in the distillation unit is preferably operated in a continuous mode, although it should be understood that batch processes are also encompassed by the present invention. Furthermore, the column(s) may be operated at greater than atmospheric pressure, at less than atmospheric pressure or at atmospheric pressure. Heat for the distillation process may be added at one or more points either by direct steam injection or indirectly via heat exchangers. The distillation unit may contain one or more points either by direct steam injection or indirectly via heat exchangers. The distillation unit may contain one or more separate beer and rectifying columns. In this case, dilute beer is sent to the beer column where it is partially concentrated. From the beer column, the vapor goes to a rectification column for further purification. Alternatively, a distillation column is employed that comprises an integral enriching or rectification section. The remaining water may be removed from the vapor by a molecular sieve resin, by adsorption, or other methods familiar to those of skill in the art. The vapor may then be condensed and denatured.

If the product to be recovered in the alcohol stream is not a distillable alcohol, such as fatty alcohols, the alcohol can be recovered by removal of alcohols as solids or as oils 182 from the fermentation vessel, thus separating from the aqueous effluent stream 184. In such an embodiment, it will be desirable to remove the lignin prior to the fermentation system as described above. In one embodiment, for example, such recovery can be carried out in a manner described in WO 2008/119082 and PCT/US07/011,923 which disclosures are herein incorporated by reference.

While the invention is susceptible to various modifications and alternative forms, specific embodiments thereof are shown by way of examples herein described in detail. It should be understood, that the detailed description thereto are not intended to limit the invention to the particular form disclosed, but on the contrary, the intention is to cover all modifications, equivalents and alternatives falling within the spirit and scope of the present invention as defined by the appended claims. The present invention will be illustrated by the following illustrative embodiment, which is provided for illustration only and is not to be construed as limiting the claimed invention in any way.

ILLUSTRATIVE EXAMPLES

General Methods and Materials

Experimental Methods
Pulping
  M&K Digester
  Wood pulping experiments were carried out in 1 L M&K digester (M/K System Inc.). Wood chips are weighed and placed in a basket, which is then inserted in the digester. The cooking liquor solution with Active Alkali (AA) charge as provided in Table 1 (Examples 1-3) is loaded in the digester and the digester is capped. The reactor is heated to reaction temperature with a residence time as indicated in the Table 1. After the reaction is complete the liquor is drawn out and the pulp is washed with cold water. Compositional analysis of the pulp is carried out to determine the sugars, lignin content and the kappa number.

3 $ft^3$ Digester
  Certain sets of wood pulping experiments were carried out in 3 $ft^3$ reactor (General Steel Tank Co., Alabama). In the pulping experiment, the cooking liquor is circulated via a recycle loop with indirect heating of liquid using electric power to conduct the experiments. Wood chips are weighed and loaded directly in the digester. The cooking liquor solution with Active Alkali (AA) charge as provided in Table 1 (Example 4) is loaded in the digester. The power to the external heater is started with the cooking liquor circulation. Digester is relieved at 100° C. to expel any non-condensable gases from the reactor. The reactor is heated to reaction temperature with a similar H-factor as determined from Table 1, Example 3. After the reaction is complete the contents of the reactor are emptied to a blow tank. Compositional analysis of the pulp is carried out to determine the sugars, lignin content and the kappa number.

Oxygen Delignification
  Oxygen delignification of high kappa pulp (as prepared by above method) was carried out in a 2.8 L reactor (Thermocraft Incorporated, NC) in an oven heated by blowing hot air. Pulp (100 g oven dried OD) was treated with 2-5% NaOH on pulp at 10% consistency under 100 psig oxygen pressure at 110° C. for 60 min (excluding time to temperature of 45 min). After delignification, the pulp was washed with cold water, centrifuged and fluffed.

Disc Refining
  The refined materials had been subjected to 5000 revolutions of refining in a PH mill (PFI mill no. 512: Hamjem Maskin AIS, Hamar, Norway) using 30 g of o.d. pulp at 10% consistency, following TAPPI procedure T248, The pulps were then filtered through a Buchner funnel with coarse filter paper under vacuum. After filtration, the pulps were fluffed and evenly placed in sealed plastic zip-loc bags in a cold room until needed.

Enzymatic Hydrolysis
  All the pulp samples were hydrolyzed using a mixture of Cellulases (Sigma, Cellulase from *Trichoderma*, resei, ATCC 2692), Xylanases (Sigma, Xylanase from *Trichoderma*, viride), and Glucosidases (Sigma, Cellobiose Novozyme 188). The reaction were conducted in 50 ml shake flask at 50° C. The pulp samples are loaded in the reactor with the solid wt % as indicated in Table 3. The pH of the system is adjusted to 4.8 using sodium acetate buffer (Aldrich). After the pH adjustment, mixture of enzymes are added in 1:0.3:0.3 ratio on volume basis. All the hydrolysis reaction were run for 96 hrs and the samples were analyzed for sugars using the HPLC method described below.

Analytical Methods
  Solids compositional analysis of the feedstock and the pulp samples were conducted by the procedure described. 0.1 gm oven dried pulp was air dried to 92%-95% consistency and added with 1.5 ml 72% sulfuric acid (Fisherbrand) in a room temperature water bath. Pulp was stirred every 15 minutes for 2 hours reaction and transferred into serum bottle containing 56 ml deionized water. Sealed with aluminum cap, serum bottle with sample solution was heated up to 120° C. at 1.25 atm pressure for 90 minutes in an Autoclave (Market Forge Inc.). Autoclaved suspension was then filtered with fine size crucible after cooling down with running tap water. Filtrate was collected and analyzed for acid soluble lignin content at 205 nm wavelength with UV-Vis spectroscope (PerkinElmer, Lambda XLS model), and residue collected in a crucible was oven (Fisher Scientific) dried for Klason lignin content analysis. The filtrate was also used for sugar analysis as described below. Component of feedstock (Example 5) and pulp samples (Example 6-9) are shown in Table 2.

The concentration of sugars (glucose, xylose, galactose, arabinose and mannose) was quantified by high-performance liquid chromatography (HPLC) system (Agilent 1200, Agilent, Santa Clara, Calif., USA) equipped with a refractive index detector on a Pb-loaded cation ex-change column of Shodex Sugar SP0810 (8×300 mm, Showa Denko, Tokyo, Japan). Prior to injection, the samples were filtered through 0.45 μm HV filters (Millipore, Bedford, Mass., USA), and a volume of 20 μL was injected. The mobile phase for the column was Milli-Q water at a flow rate of 0.5 mL/min. The system was equipped with Deashing Refill Cartridges (Bio-Rad 125-0118, Bio-Rad, Hercules, Calif., USA).

Yield was calculated as weight percentage ratio of oven dried pulp material to the total amount of feed wood chips. Kappa was measured using the TAPPI Standard T 236. H-factor is a method of expressing reaction time and temperature as a single variable, so that time and temperature (expressed in degrees Kelvin) of any cycle can be expressed as single variable. It represents the area under a curve in which relative reaction rates are plotted against time. It is expressed as following:

$$\text{H-factor} = \int_0^\tau e\left(43.2 - \frac{16.113}{T}\right) dt$$

EXAMPLES

Table 1 contains the data from all the pulping experiments (Examples 1-3) carried out in M&K digesters at various reaction times to produce varying kappa pulp. All the pulping reaction were done at 160° C. and Liquor to Wood (L:W) ratio of 4:1. High kappa pulp was then reproduced in the 3 ft$^3$ reactor (Example 4) at a similar H-factor as the M&K digester (Example 3). A portion of this high kappa pulp was separately subjected to oxygen delignification reaction (Example 5), refining (Example 6) and combination of delignification and refining (Example 7). Table 2 shows the composition of wood biomass (Example 8) and all the pulp samples (Example 9-12) prepared in examples 1, 2, 4, 5. All the substrates thus prepared were subjected to enzymatic hydrolysis at various consistencies with 5 and 20 FPU/μm solids of enzyme loadings for 96 hrs (Table 3, Examples 13-28). Total amount of glucan and xylan released as glucose and xylose respectively was measured for hydrolysis efficiency as indicated in Table 3.

TABLE 1

Pulping Experiments

| # | L:W Ratio | Temp [° C.] | Residence Time (mins) | Active Alkali (%) | Sulfidity (%) | NaOH (g/L) | Na2S (g/L) | Yield | Kappa | H-factor |
|---|---|---|---|---|---|---|---|---|---|---|
| 1 | 4 | 160 | 218 | 20 | 25 | 48.3 | 15.7 | 46.4 | 16.5 | 1300 |
| 2 | 4 | 160 | 97 | 14 | 25 | 33.8 | 11 | 60.1 | 45 | 500 |
| 3 | 4 | 160 | 82 | 10 | 25 | 24.2 | 7.8 | 63.8 | 102 | 400 |
| 4 | 4 | 160 | ~82* | 12 | 25 | 29.0 | 9.4 | — | 107 | 400 |

*Approximate time based on the H-factor similarity with Example 3.

Example 5

The higher kappa pulp (Example 4) was delignified using oxygen delignification procedure described above to prepare substrate for enzymatic hydrolysis as indicated in Table 3, Example 23-24.

Example 6

The higher kappa pulp (Example 4) was refining using the PFI mill by the procedure described above to prepare substrate for enzymatic hydrolysis as indicated in Table 3, Example 25-26.

Example 7

The higher kappa pulp (Example 4) was oxygen delignified and refined, in that order, to the prepare substrate for enzymatic hydrolysis as indicated in Table 3, Example 27-28.

TABLE 2

Compositional Analysis - Pulping Experiments

| | | Lignin | | Carbohydrates | | | | |
|---|---|---|---|---|---|---|---|---|
| Ex # | Sample | Klason | Acid Soluble | Glucan | Xylan | Mannan | Arabinan | Galactan |
| 8 | Wood | 23.6 | 3.3 | 44.2 | 18.0 | 3.1 | 1.1 | 1.5 |
| 9 | Ex. 1 | 2.3 | 1.0 | 71.6 | 17.0 | 0.9 | 0.3 | 0.7 |
| 10 | Ex. 2 | 6.5 | 1.2 | 66.5 | 17.3 | 1.0 | 0.3 | 0.8 |

TABLE 2-continued

Compositional Analysis - Pulping Experiments

| | | Lignin | | Carbohydrates | | | | |
| | | Klason | Acid Soluble | Glucan | Xylan | Mannan | Arabinan | Galactan |
|---|---|---|---|---|---|---|---|---|
| Ex # | Sample | | | | | | | |
| 11 | Ex. 4 | 14.3 | 1.7 | 60.0 | 17.5 | 1.1 | 0.5 | 0.9 |
| 12 | Ex. 5 | 10.3 | 1.4 | 65.5 | 16.8 | 1.8 | 0.2 | 0.6 |

TABLE 3

Enzymatic hydrolysis of pulp samples

| Example # | Substrate | Hydrolysis Solids Content (wt %) | Enzyme Dosage (FPU/gm Solids) | % Glucan Released (based on pulp) | % Xylan Released (based on pulp) |
|---|---|---|---|---|---|
| 13 | Ex. 1 | 5 | 5 | 76 | 89 |
| 14 | Ex. 1 | 5 | 20 | 93 | 90 |
| 15 | Ex. 2 | 5 | 5 | 76 | 83 |
| 16 | Ex. 2 | 5 | 20 | 90 | 85 |
| 17 | Ex. 4 | 5 | 5 | 75 | 79 |
| 18 | Ex. 4 | 5 | 20 | 87 | 83 |
| 19 | Ex. 4 | 10 | 5 | 43 | 53 |
| 20 | Ex. 4 | 10 | 20 | 62 | 73 |
| 21 | Ex. 4 | 15 | 5 | 44 | 55 |
| 22 | Ex. 4 | 15 | 20 | 60 | 75 |
| 23 | Ex. 5 | 5 | 5 | 81 | 86 |
| 24 | Ex. 5 | 5 | 20 | 93 | 97 |
| 25 | Ex. 6 | 5 | 5 | 77 | 80 |
| 26 | Ex. 6 | 5 | 20 | 90 | 92 |
| 27 | Ex. 7 | 5 | 5 | 84 | 87 |
| 28 | Ex. 7 | 5 | 20 | 93 | 98 |

Comparing examples 14, 16 and 18 it can be seen that enzymatic hydrolysis is inhibited with the increase in the amount of residual klason lignin. However, high levels of hydrolysis (>85%) for glucan and xylan can be achieved in all cases. There is about 10% drop in the enzymatic hydrolysis efficiency with lower loading of enzymes as indicated by results from examples 13, 15, and 17. Compared to examples in Table 4 of WO2010/060052, the substrate from the present invention process hydrolyzes with 30% better hydrolysis efficiency for glucan at 20 FPU/gm of enzymes loading. This clearly indicates that the invention process makes the pulp more susceptible for enzymatic hydrolysis compared to green liquor process. The results from examples 23-28 indicates that oxygen delignification and refining further enhances the enzymatic hydrolysis efficiency by about 5-16%. Overall, hydrolysis efficiencies of over 90% can be achieved by further treatment of the high kappa pulp. This could significantly increase the overall product yield and improve the overall economics of the process.

We claim:

1. A process for producing alcohol is provided comprising:
   (a) providing a biomass containing cellulose fibers and at least 15 weight percent of lignin;
   (b) contacting said biomass, in at least one digester, with a cooking liquor comprising 1 to 20 wt %, based on the cooking liquor, of sodium hydroxide, and water, wherein said cooking liquor having an active alkali of between 5 to 25%, and a sodium carbonate concentration of less than 3.5 wt% based on cooking liquor, at a cooking liquor to biomass ratio within the range of 2:1 to 6:1, at a temperature within the range of 100° C. to 230° C. with a residence time within 0.25h to 4h under conditions effective to provide a pulp stream containing pulp having a lignin content of 5% to 20% by weight, based on the pulp, and a chemical liquor stream containing sodium compounds;
   (c) washing the pulp stream with a water stream thereby removing at least a portion of lignin and hemicellulosic material and producing washed pulp stream;
   (d) hydrolyzing the washed pulp stream by treating the streams with an enzyme solution comprising cellulases and optionally xylanases at a pH within the range of about 3 to about 7 at a temperature within the range of 30° C. to 90° C. to produce a hydrolyzate containing from about 4% to 30% by weight of fermentable sugar;
   (e) fermenting the hydrolyzate in the presence of a microorganism at a temperature with the range of about 25° C. to about 55° C. at a pH within the range of about 4 to about 6 thereby producing an alcohol stream containing at least one alcohol having 2 to 18 carbon atoms; and
   (f) recovering at least one of said alcohol from the alcohol stream.

2. The process of claim 1 further comprising concentrating the washed pulp stream from step (c) by mechanical dewatering prior to contacting the washed pulp stream with cellulases in step (d) thereby increasing solids content of the washed pulp stream from 15 to 40 wt % solids.

3. The process of claim 1 further comprising subjecting the washed pulp stream to oxygen delignification prior to contacting the washed pulp stream with cellulases in step (d).

4. The process of claim 1 further comprising mechanically refining solids in the washed pulp stream prior to contacting the washed pulp stream with cellulases in step (d), thereby reducing the solids in size.

5. The process of claim 2 further comprising subjecting the thus-concentrated washed pulp stream to oxygen delignification prior to contacting the washed pulp stream with cellulases in step (d).

6. The process of claim 2 further comprising subjecting the thus-concentrated washed pulp stream to mechanically refining solids in the washed pulp stream prior to contacting the washed pulp stream with cellulases in step (d), thereby reducing the solids in size.

7. The process of claim 2 further comprising subjecting the thus-concentrated washed pulp stream to oxygen delignification and mechanically refining solids in the washed pulp stream prior to contacting the washed pulp stream with cellulases in step (d), thereby reducing the solids in size.

8. The process of claim 1 further comprising subjecting the washed pulp stream to oxygen delignification and mechanically refining solids in the washed pulp stream prior to contacting the washed pulp stream with cellulases in step (d), thereby reducing the solids in size.

9. The process of claim 1 wherein in step (c) the water stream is flowing countercurrent to the pulp steam.

10. The process of claim 1 further comprising (g) removing at least a portion of the lignin from one of washed pulp stream, hydrolyzate, or alcohol stream prior to step (d) or (e) thereby providing a washed pulp stream, hydrolyzate, or alcohol stream containing less than 5% lignin content based on said stream.

11. The process of claim 1 further comprising, (h) concentrating the chemical liquor stream from step (b) to produce a concentrated chemical liquor stream, (i) burning said concentrated chemical liquor stream to produce a chemical recycle stream, (j) recausticizing said chemical recycle stream to produce a cooking liquor feed stream, and (k) recycling the cooking feed stream to the digester in step (b) as at least a portion of the cooking liquor.

12. The process of claim 11 further comprising (1) removing at least a portion of the lignin from the aqueous effluent stream to produce an aqueous effluent recycle stream which is recycled through the chemical recycle stream.

13. The process of claim 1 where the cooking liquor has a pH from 10 to 14.

14. The process of claim 1 wherein the cooking liquor comprises 4 to 20 wt %, based on the cooking liquor, of sodium hydroxide.

15. The process of claim 14 wherein the cooking liquor has a sulfidity in the range from about 15% to about 40%.

16. The process of claim 15 wherein the cooking liquor further comprises anthraquinone, sodium borate and/or polysulfides.

17. The process of claim 1 wherein the active alkali is the range of 10 to 20%.

18. The process of claim 1 wherein the cooking liquor to biomass ratio is within the range of 3:1 to 5:1.

* * * * *